United States Patent [19]
Foster

[11] Patent Number: 5,802,832
[45] Date of Patent: Sep. 8, 1998

[54] TEXTURING YARN

[75] Inventor: Peter William Foster, Alderley Edge, England

[73] Assignee: University of Manchester Institute of Science and Technology, Manchester, United Kingdom

[21] Appl. No.: 284,495
[22] PCT Filed: Feb. 5, 1993
[86] PCT No.: PCT/GB93/00245
   § 371 Date: Oct. 3, 1994
   § 102(e) Date: Oct. 3, 1994
[87] PCT Pub. No.: WO93/16218
   PCT Pub. Date: Aug. 19, 1993

[30] Foreign Application Priority Data

Feb. 5, 1992 [EP] European Pat. Off. ............. 9202397

[51] Int. Cl.$^6$ .................................................. D01H 7/46
[52] U.S. Cl. ............................ 57/264; 28/248; 28/249; 57/93; 57/284; 57/287; 57/289; 57/290
[58] Field of Search ...................... 57/282, 284, 287, 57/288, 289, 290, 264, 93, 332; 28/248, 249

[56] References Cited

U.S. PATENT DOCUMENTS

| | | | |
|---|---|---|---|
| 3,802,038 | 4/1974 | Bauch et al. .............................. | 28/248 |
| 4,050,225 | 9/1977 | Anahara et al. . | |
| 4,135,511 | 1/1979 | Nikkel ....................................... | 28/248 |
| 4,369,555 | 1/1983 | Nikkel ....................................... | 28/248 |
| 4,383,404 | 5/1983 | Pascoe ...................................... | 57/284 |
| 4,398,386 | 8/1983 | Endo et al. ............................... | 57/288 |
| 4,456,818 | 6/1984 | McCollough et al. .................... | 57/284 |
| 4,720,702 | 1/1988 | Martens .................................... | 340/677 |
| 4,888,945 | 12/1989 | Maeda et al. ............................. | 34/1.8 |
| 5,048,281 | 9/1991 | Dallman et al. .......................... | 57/264 |
| 5,189,810 | 3/1993 | Vetter ........................................ | 57/264 |
| 5,369,945 | 12/1994 | Wessolowski et al. ................... | 57/264 |
| 5,440,870 | 8/1995 | Neumann .................................. | 57/265 |
| 5,502,961 | 4/1996 | Tone et al. ................................ | 57/264 |

FOREIGN PATENT DOCUMENTS

| | | |
|---|---|---|
| 0143974 | 6/1985 | European Pat. Off. . |
| 0207471 | 1/1987 | European Pat. Off. . |
| 0271252 | 6/1988 | European Pat. Off. . |
| 439183 | 7/1991 | European Pat. Off. . |
| 469763 | 2/1992 | European Pat. Off. . |
| 3811437 | 10/1988 | Germany . |
| 3938183 | 5/1991 | Germany . |
| 841255 | 7/1960 | United Kingdom . |

*Primary Examiner*—William Stryjewski
*Attorney, Agent, or Firm*—Cushman Darby & Cushman IP Group of Pillsbury Madison & Sutro LLP

[57] ABSTRACT

A method of controlling the manufacture of false twist textured yarn characterised by adjusting non-isothermally in a closed loop the heat flux taken up by the yarn in tension to a specific yarn dyeability. Adjustment can be achieved by feeding back the output of a direct-acting yarn texture sensor to control at least one of yarn heater heat supply, yarn twist speed and yarn feed speed. The sensor is arranged to sense at least one of textured yarn speed, yarn temperature, yarn bulk and yarn tension. A very compact texturing line is possible when the control method is applied.

31 Claims, 3 Drawing Sheets

TEXTURING YARN

BACKGROUND OF THE INVENTION

This invention relates to the manufacture of yarn by the false twist texturing method in which a multistrand synthetic yarn is given a false twist and heated to "texture" or "bulk" the yarn. Among other advantages "texturing" improves the feel of garments made from the yarn.

Typically a very large machine is needed for texturing yarn. This machine includes numerous similar portions, sometimes as many as 216, in each of which yarn is textured. The portions are known as "positions" and each position has a supply of yarn to be textured, a texturing apparatus and a take-up for the textured yarn. Each texturing apparatus is some six metres high with heating and cooling zones some two to three metres long and subject to varying ambient conditions. All the positions are intended to operate at the same texturing conditions and all are supplied with the same type of yarn. In theory the whole machine will operate at the same conditions and each position will produce yarn which is textured in the same way. However, in such a large machine the conditions will not always be the same from position to position and variations in texturing are inevitable despite careful design and constant attention to operation. In particular the heating arrangement is inflexible and it is appropriate to classify such machines as isothermal, also recognising the aim of an identical heat state at each position. Despite the above developments the need for more economic manufacture demands improvements above the speed and quality now achieved. In particular the dyeability of the yarn can vary due to inconsistency of yarn texturing input and this can lead to the rejection and waste of much material.

In EP-A-20143974 (Teijin Ltd) there are suggestions for an isothermal method of producing textured polyester yarn in which the heater length can be reduced to less than 1.8 metres. Specifically a heater length of 0.65 to 0.70 metres with a yarn speed of 400 metres per minute and a straight line path is proposed. However the method requires a special heater called a "non-touch" type with a bow shaped yarn path in which the yarn is guided by plates with shaped slits to suppress a yarn balloon. The heater temperature is from 300° C. to 800° C. If the yarn breaks in the heater it will be destroyed by the very high temperature of the heater burning off the yarn. The very high temperature is needed as heat is transferred to the yarn by radiation in an open environment so heat loss is high. Because the yarn must not touch the heater the yarn must be "lifted off" during start-up and similar interruptions to continuous running.

In U.S. Pat. No. 4888945 (Murata), and equivalent DE-A-3811437, a quality control technique for a conventional yarn texturing apparatus is described which avoids harm to yarn quality which can be caused by testing yarn during production. The technique is based on measurements made while yarn is being wound onto the empty bobbins when first loaded to replace bobbins doffed with full packages.

EP-A-20271252 (Rieter Scragg) describes a conventional isothermal yarn texturing apparatus to which a monitoring method is applied. This monitoring method involves measuring the difference in crimped yarn velocity when under high tension (velocity V1) and low tension (velocity V2). The quantity V1−V2×100 is defined as the crimp velocity and is stated to V1 have a positive relationship to the crimp retraction quantity.

GB-A-841255 (Dunlop) describes an apparatus for determining the change in length under load of a length of filamentary material travelling from one point to another. Lengths of material under zero and known tension are compared in percentage terms to give extensibility of the material.

SUMMARY OF THE INVENTION

It is an object of the present invention to provide an improved yarn texturing production technique.

According to the invention there is provided a method of controlling the manufacture of false twist textured yarn characterised by adjusting non-isothermally in a closed loop the heat flux taken up by the yarn in tension to a specific dyeability.

In particular the method permits compensation for the effects of yarn tension and shrinkage variation in a supply package on texturing.

The method permits variation of texturing conditions in a single position. The method permits in a multiple position machine variation from one position to another so that different texturing conditions exist in individual positions at the same time. In this way, if required, the specific dyeability can be achieved from all the positions at the same time by providing appropriately different conditions.

The adjustment in a closed loop may be under a control signal generated by one of a yarn tension sensor, a yarn temperature sensor, a yarn driven drum sensor.

A relaxation of yarn tension may be caused immediately downstream of the sensor.

The heat flux take up may be adjusted by adjusting the heat flux supply in terms of temperature, pressure or fluid specific heat. The heat flux may be adjusted by use of a main and an auxiliary heater.

The heat flux take up may be adjusted by adjusting at least one of the twist level and the speed of the yarn.

According to a particular aspect of the invention there is provided a method of false twist texturing a yarn including:

providing a supply of yarn to be textured and take-up means for textured yarn, establishing a tensioned feed path for yarn to be textured between the supply and the take-up, providing in said feed path an input yarn drive, a yarn texturing stage, a textured yarn sensor giving a sensor output, an output yarn drive and a drive for the take-up means, causing a relaxation of yarn tension at the sensor, further providing yarn heater control means, and drive control means, linking the textured yarn sensor in a control arrangement to at least one of the yarn texturer and the yarn drives, whereby yarn texture is maintained by response of the sensor to provide said output to operate the control arrangement.

The yarn texturing stage may include a yarn heater, a yarn cooler and a yarn twister and twister drive.

The method may include providing the yarn heater in the form of a main heater and an auxiliary heater, each with a respective control means, linking the textured yarn sensor output with the auxilliary heater control means in said control arrangement, and causing or permitting the control arrangement to adjust the auxilliary heater in response to the sensor output.

The method may include providing a heater having a high intensity heat flux. A jet or tube heater fed with hot fluid may be used as the high flux heater for yarn passed through it.

The fluid may be heated by passing it over a main heater and an auxiliary heater, each fluid heater having control means incorporated in the control arrangement. The method may include controlling the flow of the heated fluid by the control arrangement.

The method may include providing the textured yarn sensor as a yarn speed sensor.

The relaxation of yarn tension may be caused immediately downstream of the sensor. The relaxation may be caused by a yarn tensioner immediately downstream of the sensor and before the output yarn drive. The method may include providing the textured yarn sensor as a yarn tension sensor between the intermediate yarn drive and the output yarn drive, with said relaxation adjacent the sensor.

The method may include providing the yarn twister and drive with a speed control, linking the textured yarn sensor output with the yarn twister drive speed control in said control arrangement, and causing or permitting the control arrangement to adjust the yarn twister speed in response to the sensor output.

The method may maintain a yarn texturing regime of yarn speed, yarn twister speed and yarn heater temperature, while varying at least one of yarn twister speed and yarn heater temperature.

The method introduces texture into the heated yarn by sending yarn twist back up the feed path to the yarn in the heater. The texture is set by heating the yarn followed by cooling in the twisted state to below the second order transition temperature.

When one of the yarn twister drive speed and yarn heater are controlled in the control arrangement in response to the yarn sensor output the other may be kept constant.

Heat may be provided to the yarn heater and any auxiliary heater by any convenient hot fluid or a mixture of fluids. The hot fluid may be superheated (dry) steam or hot compressed air. The texturing regime may be maintained to a set drive speed, for example 2500 rpm ± 15 rpm.

The steam may be dried at 300° C.

The feed path is preferably substantially straight and may be in a vertical or a horizontal line.

According to another aspect of the invention there is provided a method of texturing yarn including providing a supply of yarn to be textured and take-up means for textured yarn, establishing a feed path for yarn to be textured between the supply and the take-up, moving yarn from said supply into said feed path, drawing, heating and twisting yarn in the feed path to form textured yarn, moving the textured yarn along the feed path to the take-up means causing the textured yarn to drive a yarn speed sensor, causing or permitting a yarn relaxation immediately downstream of the sensor, deriving from said sensor a control signal including a yarn speed component, applying the control signal to at least one of the driving of the yarn, the drawing of the yarn, the twisting of the yarn and the heating of the yarn, whereby a selected yarn texture is maintained.

The method may achieve false-twist texturing of undrawn, partially drawn and drawn yarn.

The invention also provides apparatus to achieve control of yarn texture by feedback of the output of a direct-acting yarn texture sensor to control at least one of yarn heater heat supply, yarn twist speed and yarn feed speed. The sensor may sense at least one of textured yarn speed, yarn tension, yarn temperature and yarn bulk. The relaxation of yarn desirably has unimpeded effect on the sensor.

BRIEF DESCRIPTION OF THE DRAWINGS

Embodiments of the invention will now be described with reference to the accompanying drawings in which FIG. 1a shows a detail of part of FIG. 1.

DESCRIPTION OF THE PREFERRED EMBODIMENT

Figure 1:
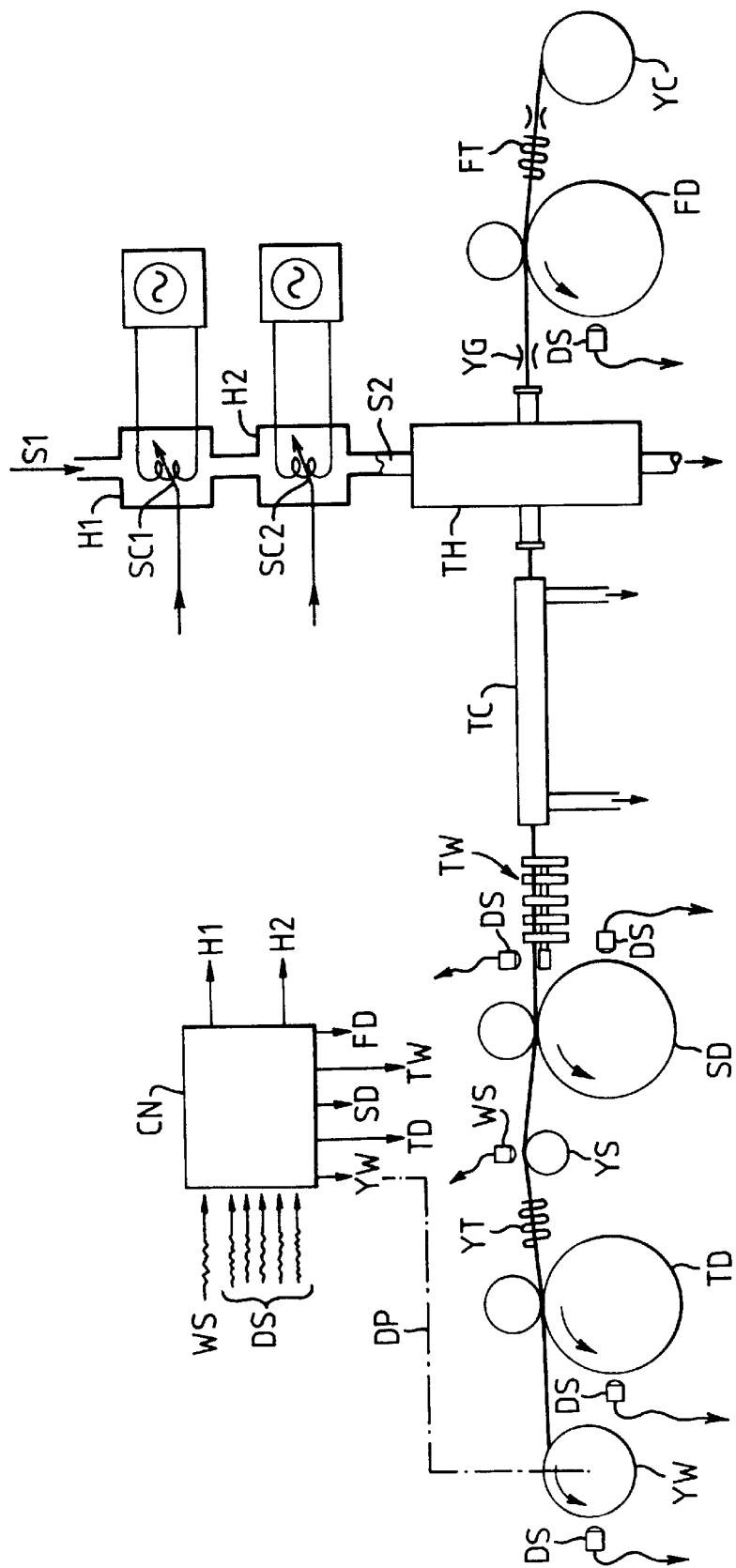
FIG. 1 shows an outline of a yarn texturing line embodying the invention.

As shown in FIG. 1 the yarn texturing line is straight from yarn supply to yarn take-up. In other embodiments the line can be other than straight, for example folded through a right angle between the heating and cooling stages, but the straight form has several advantages and as a texturing line embodying the invention need not be very long, and not as long as in the prior art, there is not the need to fold the line as in the prior art high speed machines.

In broad terms the line includes the following stages, a yarn supply (YC), a first yarn drive (FD), a yarn textured heater (TH) using steam in a heating jet, a cooler (TC) to set the textured yarn, a twisting device (TW), a second yarn drive (SD), a yarn speed sensor (YS), yarn tensioner (YT) a third yarn drive (TD) and a yarn winder (YW). The line is provided with steam supply (S1) for the texturing heater to produce a high and rapidly adjustable heat flux to the yarn. The line conveniently includes five separate drive means, e.g. electric motors with respective speed sensors (DS, FIG. 3) and respective controlled power supply and control means (CPS, FIG. 3) for each yarn drive means. The five motors are one for each of the three yarn drives, one for the yarn twister and one for the yarn winder. The yarn drives are conveniently a main drum on the shaft of the motor with a small drum on a jockey arm urged against the main drum. Yarn may be taken once or twice round the small drum and another pulley if required. A control arrangement, CN, shown in more detail below, is provided for the whole line.

The yarn speed sensor YS is a very important element as accurate speed sensing is part of the control of the line and the sensor supplies a yarn speed signal for feedback to control at least one of yarn treatment temperature or the drives in a coordinated manner. The shaft speeds of the twister and the drive motors are measured by means of a slotted disc mounted on the relevant shafts and fitted with photoelectric sensors.

Figure 2:
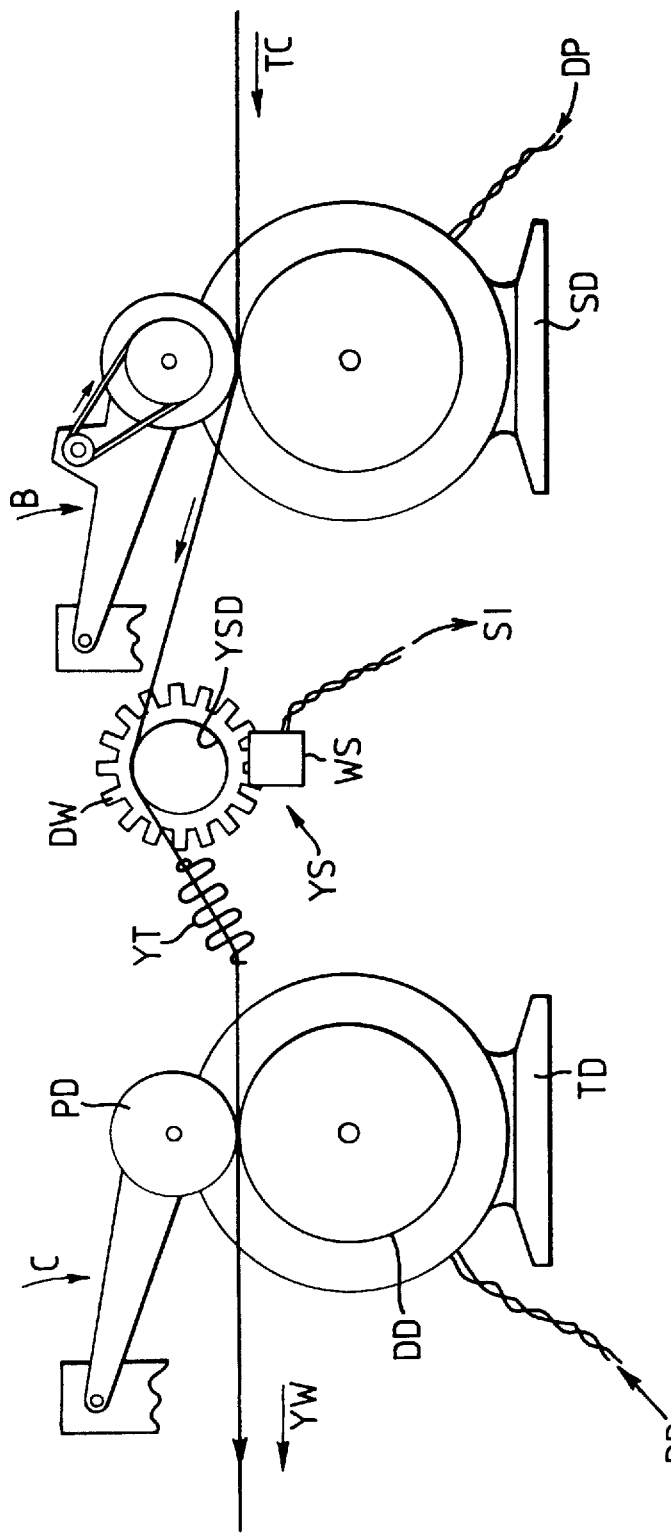
FIG. 2 shows in more detail a yarn speed sensor.

FIG. 2 shows a form of yarn speed sensor found very suitable in an embodiment of the invention. The second yarn drive SD draws yarn from the twister TW and feeds it forward over a freely rotatable drum YSD in the yarn speed sensor YS. The third yarn drive TD draws yarn from off the drum YSD through a yarn tensioner YT and feeds the yarn forward to the yarn winder YW. The drum YSD is freely rotatable at very high speed, corresponding to a yarn speed of some 2000 metres per minute or more, on a well-supported shaft which also carries a slotted disc DW forming part of a speed sensing arrangement for the drum. A photo-electric device WS is arranged to detect the rotation of the slotted disc to produce a drum speed related pulse signal SI as sensor output. In operation to sense yarn speed yarn is wrapped only part-way round the drum and yarn tension controlled to achieve very little slippage so that accurate speed sensing is provided. Conveniently about 30° wrap angle on the drum is used, the drum being about 40 millimetres in diameter. Greater amounts of wrap, including at least one full turn, may be used. The effect of the downstream tensioner device YT is needed to achieve suitable results from the speed sensor, however the effect may be produced by other means, for example, eddy current braking of the drum of the sensor through such action on the disc DW. The eddy current braking may be variable by control action of the control system to vary the effect of the tension device. The nature of the effect is a slight reduction or relaxation of yarn tension at the sensor compared with tension elsewhere in the line, for example at drive C.

As so far described a very accurate yarn speed sensor YS has been provided. Similar slotted disc and photoelectric drive sensors are suitable for drive sensors DS.

Returning again to FIG. 1 upstream from the sensor is the yarn texturing region. Yarn from the supply YC is fed through a guide YG and a tensioner FT to the yarn texturing heater TH by the action of the first yarn drive FD drawing the yarn from the supply and feeding it to the texturing heater in a controlled manner.

The texturing heater is supplied with steam which has come from a boiler over a superheating arrangement which has two heating sections, a first, main, superheater H1 and a second, auxiliary, heater H2. The first heater receives dry steam (S1), which may already be superheated, and heats this as needed to produce steam at a controlled (SC1) base temperature a little below that required to texture the yarn. The second, auxiliary, heater receives the dry superheated steam from heater H2 and is readily controllable (SC2) to heat the steam as needed so that the actual texturing temperature can be adjusted rapidly in a small range from the base temperature (set below the expected minimum texturing temperature) upwards to beyond the expected maximum texturing temperature. Advantageously the first heater H1 is controlled or adjusted so that the second heater H2 is at about 50% of power at the nominal setting of the texturing line. The main and supplemental heaters are conveniently electrically energised, as indicated by the conventional symbols. The second heater clearly must have a small thermal mass to assist rapid response, also quick acting controls for this heater are needed. Other hot fluids may be used, e.g. hot compressed air or a mixture, such as air and steam.

In one embodiment the yarn texturing heater TH is similar to the structure used in an earlier texturing process. The particular form of heater is shown in general form in FIG. 1a but it is emphasised that other forms of yarn texturising heater which achieve the heat flux for takeup by the yarn may be used.

In the scrap-section of TH in FIG. 1 the flow of steam from the heaters H1 and H2 is identified at S2. The yarn enters the heater TH through an arrangement to resist escape of steam. The yarn passes through a chamber CH to which the steam supply S2 is admitted and the yarn and steam leave the chamber CH, the yarn being textured (not shown) in the process and the steam passing to any convenient exhaust or recovery ER.

In the yarn heater (TH) the yarn is heated by the heater, generally to above the second transition temperature, by being brought into intimate contact with a flow of heated fluid under pressure. From the yarn heater the yarn is supplied to a cooler TC of a water cooled trough through which the yarn is drawn by yarn drive SD to ensure cooling below the second transition temperature. At the outlet of the cooler trough TC is a false twister TN driven at a controlled speed, which is conveniently variable.

The exact order and arrangement of the main and auxiliary heaters may be altered while retaining the specified action, as will now be apparent to those skilled in the art.

Various fluids may be mixed in a controlled manner to alter the effective specific heat of the fluid providing the heat flux.

As now described yarn is supplied in a controlled manner to a closely controlled steam heater to be textured, and drawn through a cooler then a twister and moved onwards to be fed to an accurate yarn speed measuring stage to be then wound in any convenient manner but at a controlled speed. The twister causes the twist to travel back along the yarn to the first drive FD, although in some cases fluid in the heater can affect this twist travel, and even bring about pre-texturing. The first drive sets the speed of the line.

A further important feature of the technique is that the auxiliary heater can be controlled in dependence on measured yarn speed to achieve a consistent required yarn quality, particularly important for consistent dyeability.

The operating parameters of one embodiment of the invention are indicated by the following results of measurements on the equipment. (Yarn temperature was measured with a non-contact oscillating horizon pyrometer.):

|   |   | Yarn temperature (°C.) |
|---|---|---|
| I | Stem pressure (psi) | |
|   | 90 | 200 |
|   | 100 | 199 |
|   | 120 | 202 |
|   | 140 | 204 |
| II | Texturing steam temperature (°C.) | |
|   | 230 | 175.5 |
|   | 240 | 183.5 |
|   | 250 | 189.5 |
|   | 260 | 196.5 |
|   | 270 | 200 |
|   | 280 | 204 |

The properties of the yarn produced are indicated by the following measurements:

| Material: POY polyester 300f 30 to 167f 30 | | | |
|---|---|---|---|
| III (Temperature 220° C.) | | | |
| Pressure (psi) | T (CN/Tex) | E (%) | Bulk (K %) |
| 70 | 35.5 | 20.2 | 31.5 |
| 85 | 34.6 | 19.0 | 33.7 |
| 100 | 35.4 | 18.7 | 33.0 |
| 115 | 35.2 | 19.3 | 40.2 |
| 130 | 35.1 | 18.9 | 39.1 |
| IV (constant pressure) | | | |
| Temperature (°C.) | T (CN/Tex) | E (%) | Bulk (K %) |
| 200 | 34.7 | 19.6 | 29.8 |
| 210 | 35.1 | 19.2 | 30.4 |
| 220 | 35.4 | 18.7 | 32.8 |

-continued

Material: POY polyester
300f 30 to 167f 30

| | | | |
|---|---|---|---|
| 230 | 35.5 | 19.2 | 37.4 |
| 240 | 35.2 | 19.0 | 41.5 |
| 250 | 36.1 | 19.4 | 41.9 |

V Dye uptake, Crimp centration
(10 readings at each point)

| Texturing Temperature | | Dye uptake | Yarn contraction | |
|---|---|---|---|---|
| Nominal (°C.) | Variation | (K/S) | % CV | (%) % CV |
| 200 | ±8.5 | 16.2 | 3.2 | 29.8 0.9 |
| 250 | ±7.0 | 11.0 | 3.0 | 45.5 0.6 |

It will be noted from the above that in one embodiment of the invention the auxiliary heater is controlled in dependence on the measured yarn speed and a control arrangement is provided to achieve this. In other embodiments drive speed alone or drive speed and heating may be so-controlled to achieve an adequate control of yarn quality.

For a given yarn supply and texturing requirement a yarn speed is identified for which steam or other hot fluid conditions are selected. The texturing line is then run and when a yarn speed change is sensed steam conditions are altered to reverse the yarn speed change, maintaining the required texturing. This is on the basis that a primary cause of yarn speed change is believed to be a change of texturing which affects the relaxation of the yarn at the yarn speed sensor. The temperature of the yarn exiting from the heater is also usable as the basis of the control of texturing.

Figure 3:
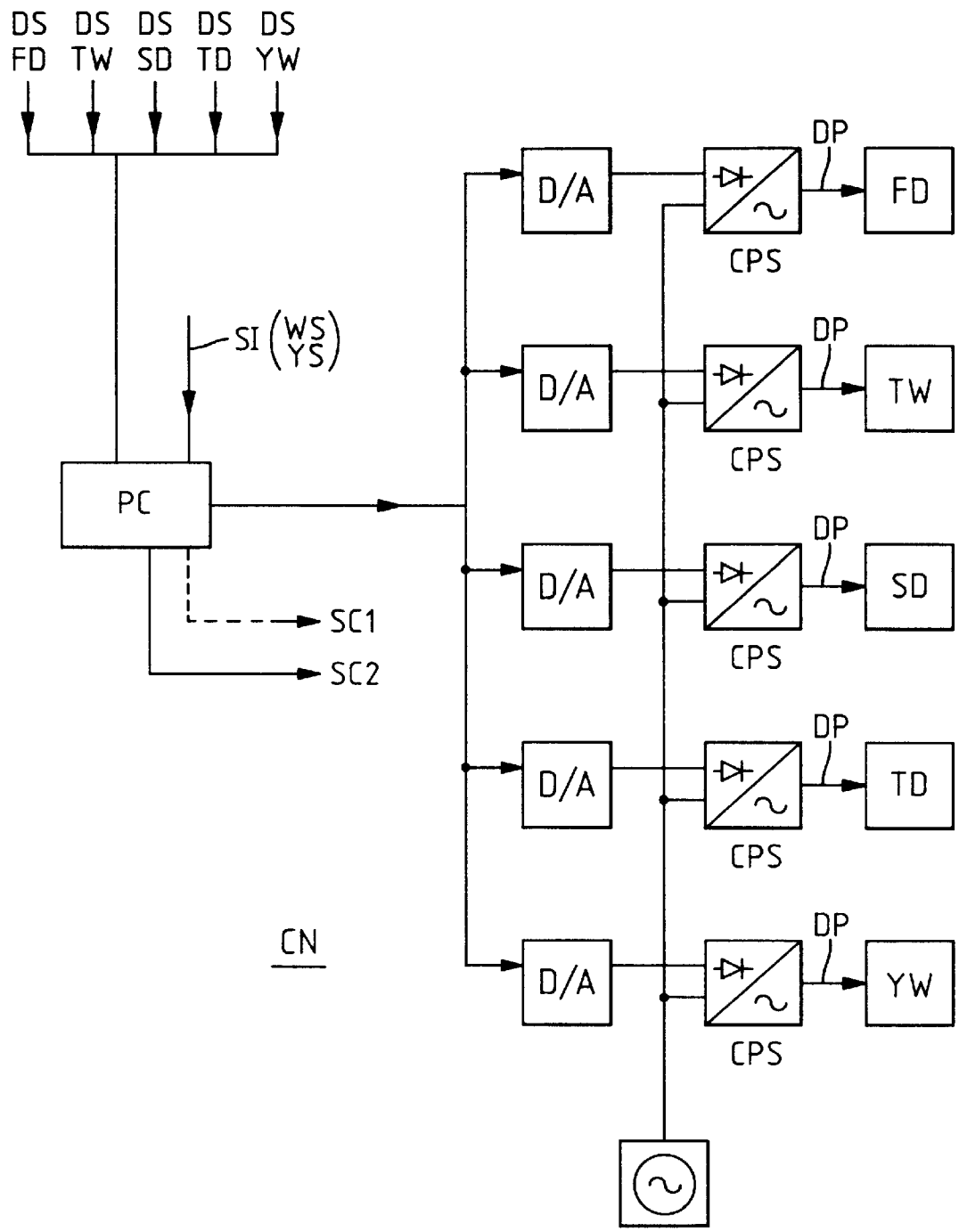
FIG. 3 shows in outline a control arrangement circuit.

FIG. 3 shows in outline a control arrangement of a feedback loop including a small computer PC to carry out the appropriate calculations from the information (SI) supplied from the yarn speed sensor (YS) and the respective drive speed sensors (DS) to provide control information to the respective inverters driving each drive motor with drive power DP. Those skilled in the art will be aware of the conventional techniques available to provide such an arrangement.

Preferably the speeds of drives FD, SD and TD are established in a particular relationship (not always equal speeds) for a required yarn texturing action and kept in this relationship while texturing is adjusted to the required action by control of heating and/or twist and /or speed.

Two examples of the control of yarn texturing in accordance with the invention are as follows, the yarn being 167 dtex (34 fils) polyester yarn with steam at 100 psi pressure and approximately 200° C. (the speeds are rounded values):

| | | | |
|---|---|---|---|
| Nominal yarn throughput speed (m/min) | | 600 | 800 |
| Feed roller (m/min) | FD | 556 | 769 |
| False twist motor (rpm) | TW | 7136 | 9514 |
| First output roller (m/min) | SD | 600 | 800 |
| Second output roller (m/min) | TD | 598 | 798 |
| Take-up drive (m/min) | YW | 569 | 757 |

In one arrangement the steam heater has a main heater with a rating of some 2.5 KW and an auxiliary heater with a rating of some 800 W. Each heater has a semiconductor power controller. For the main heater the setting can be controlled in accordance with a look-up table for yarn type and texturing and will typically be at about 1 KW. The auxiliary heater is controlled continuously at a rate of a few cycles/second to a few tens of cycles/second. Typically the auxiliary power level is about 400 W. The power supply is conveniently at mains potential, say 110 or 240 volts ac. If heated air is used the temperature will be some 200° C. to 220° C., depending on the yarn.

As described above the yarn sensor is a yarn speed sensor but a yarn tension sensor giving an appropriate output is also suitable. The change in textured yarn speed speed or tension when the drive conditions for drives FD, SD and TD are accurately maintained constant indicates that yarn texturing has deviated from a desired set condition. Other sensors are possible as the source of control information for the closed loop control of heat flux taken up by the yarn, for example yarn bulk or yarn temperature at the heater exit.

Earlier attempts to make the machines smaller of necessity means the use of small heaters, which in turn means that the heaters have to be of a high intensity. The high intensity means that either they have to be so hot that they melt the yarn if there is a yarn breakage, or they have to be of tubular or jet design with narrow orifices using hot fluid under pressure. The narrow orifices quickly change in dimension with time, due to the deposition of spin finish and oligomer and so the heat transfer characteristics of the heater change. The above techniques correct for these and other changes in heating characteristics so as to permit the use of small high intensity heaters which transfer a constant amount of heat (heat flux) to the yarn (albeit by altering the temperature of the fluid in the jet as the flow rate of the fluid changes due to changes in the sizes of the orifices), which in turn permits the use of short threadlines which in turn, due to the reduction in surging, permits the use of much higher speeds than current large machines. This also achieves the important result of consistent dyeability. While smaller heaters are made possible by the invention the techniques of the invention need not be restricted to such heaters. The use of controlled heaters in closed loops provides for non-isothermal operation of a multiple position machine when modified as will be apparent to those skilled in the art in view of above disclosed techniques.

The technique is described for a horizontally arranged feed path but a vertical path is also possible and will be much more compact and economical than the current technology using extended heaters and coolers. The accurate sensing of the textured yarn condition such as speed or tension permits the degree of texturing to be assessed continuously and continuous on-line maintenance of required texturing to be achieved by control of yarn drive speeds and/or texturing conditions. In particular consistency of dyeability of textured yarn produced from a specific supply of yarn can be achieved even when the yarn is textured in several positions in a machine.

I claim:

1. A method of manufacturing a textured yarn comprising the steps of:
    feeding a yarn to be textured from a supply thereof to a take-up means for the textured yarn along a path including a texturing zone;
    false twisting the yarn so that it is twisted in the texturing zone;
    heating then cooling the twisted yarn in the texturing zone to produce a false twist textured yarn;
    sensing a condition of the yarn at a position in said path;

providing adjustability of at least one of said feeding, false twisting and heating and cooling steps; and adjusting at least one of said steps for which adjustability is provided in accordance with the condition sensed in said sensing step, wherein the condition sensed in said sensing step comprises yarn speed while tension in the textured yarn is relaxed at a position in said path between the texturing zone and the take-up means.

2. A method according to claim 1, wherein tension in the yarn is relaxed by overfeeding the yarn.

3. A method according to claim 2, wherein the tension-relaxed yarn runs over a freely-rotatable drum, wherein a speed of the yarn is sensed photoelectrically.

4. A method according to claim 1, wherein the heating step being effected by a hot fluid.

5. A method according to claim 4, wherein the hot fluid comprises steam.

6. A method according to claim 4, wherein the hot fluid comprises hot air.

7. A method according to claim 4, wherein the temperature of the hot fluid is adjusted in accordance with the condition sensed.

8. A method according to claim 7, wherein the temperature of the hot fluid is adjusted by a rapid response heater.

9. A method according to claims 7, wherein the temperature of the hot fluid is adjusted by a main heater and a supplemental rapid response heater.

10. A method according to claim 1, wherein said feeding step is controlled by feeding the yarn by speed-controllable feed rollers, wherein a speed of at least one feed roller is controlled in accordance with the condition sensed in said sensing step.

11. A method according to claim 1, wherein said false twisting step is controlled by false twisting the yarn with a rotating false twist device and the speed of the false twist device is adjusted in accordance with the condition sensed in said sensing step.

12. A method according to claim 1, comprising adjusting at least one of said steps for which adjustment is provided by a closed loop feedback control arrangement in order to maintain the condition sensed constant.

13. A method for texturizing a yarn comprising:

feeding the yarn under tension-from a source to a take-up therefor along a path, said path including a false twist zone;

heating and cooling the yarn in said false twist zone while the yarn is highly twisted thereby texturizing the yarn; and controlling a processing parameter effecting the texture of yarn in the false twist zone, said processing parameter being controlled in accordance with the result of a measurement made on the yarn travelling along said path after leaving the false twist zone, said measurement being indicative of the effect of the texturizing on the yarn, wherein the measurement is indicative of the dyeability of the texturized yarn.

14. A method according to claim 13, in which measurement is made on the yarn in tension-relaxed conditions between the false twist zone and the take-up.

15. A method according to claim 13, in which the yarn drives in rotation a freely-rotatable drum, wherein a speed of the yarn is sensed as the measurement.

16. A method according to claim 15, in which the speed is sensed photoelectrically.

17. A method according to claim 13, in which measurement is made on the yarn in the false twist zone.

18. A method according to claim 17, in which yarn temperature on leaving a yarn heater is measured as an indication of heat take-up by the yarn.

19. A method according to claim 13, in which the measurement is used to control the processing parameter in a closed-loop control system.

20. A method according to claim 13, in which the measurement is used to control yarn heating.

21. A method according to claim 20, in which yarn heating is effected by direct heat exchange with a hot fluid, wherein the fluid temperature is controlled in accordance with the measurement.

22. A method according to claims 21, in which the fluid is heated in main and auxiliary heaters of which the auxiliary heater is controlled.

23. A method according to claim 13, in which the measurement is used to control yarn tension in the false twist zone.

24. A method according to claim 23, in which yarn tension is controlled by controlling the speed of at least one yarn feed roller.

25. A method according to claim 13, in which the measurement is used to control yarn twist level in the false twist zone.

26. A method according to claim 25, in which the twist level is controlled by controlling the speed of rotation of a rotary false twist device.

27. A method for texturizing a yarn comprising:

feeding the yarn under tension from a source to a take-up therefor alone a path, said path including a false twist zone;

heating and cooling the yarn in said false twist zone while the yarn is highly twisted thereby texurizing the yarn; and controlling a processing parameter effecting the texture of the yarn in the false twist zone, said processing parameter being controlled in accordance with the result of a measurement made on the yarn travelling along said path after leaving the false twist zone, said measurement being indicative of the effect of the texturizing on the yarn, wherein the measurement is indicative of the bulk of the texturized yarn.

28. A method according to claim 27, in which the measurement is used to control yarn heating.

29. A method according to claim 28, in which yarn heating is effected by direct heat exchange with a hot fluid, wherein the fluid temperature is controlled in accordance with the measurement.

30. A method according to claim 29, in which the fluid is heated in main and auxiliary heaters of which the auxiliary heater is controlled.

31. A method according to claim 27, in which the measurement is used to control yarn tension in the false twist zone.

* * * * *